United States Patent [19]

Patsidis et al.

[11] Patent Number: 5,347,026
[45] Date of Patent: Sep. 13, 1994

[54] FLUORENE COMPOUNDS AND METHODS FOR MAKING

[75] Inventors: Konstantinos Patsidis; H. G. Alt, both of Bayreuth, Fed. Rep. of Germany; Syriac J. Palackal, Bartlesville, Okla.

[73] Assignee: Phillips Petroleum Company, Bartlesville, Okla.

[21] Appl. No.: 75,931

[22] Filed: Jun. 11, 1993

[51] Int. Cl.$^5$ ............................ C07F 7/02; C07F 7/22; C07F 7/30
[52] U.S. Cl. ........................................ 556/87; 556/95; 556/400; 556/465; 556/466; 556/478
[58] Field of Search ................... 556/87, 95, 400, 465, 556/466, 478

[56] References Cited

U.S. PATENT DOCUMENTS 5,191,132   3/1993   Patsidis et al. .................. 585/375
5,210,352   5/1993   Alt et al. ........................ 585/375

OTHER PUBLICATIONS

Manipulation of Organoactinide Coordinative Unsaturation. Synthesis, Structures and Reactivity of Thorium Hydrocarbyls and Hydrides with Chelating Bis(tetramethylcyclopentadienyl) Ancillary Ligands, *Organometallics* 1988, 7, pp. 1828–1838 Application 734,853, filed Jul. 23, 1991, S. Palackal et al.

*Primary Examiner*—Jose' G. Dees
*Assistant Examiner*—Porfirio Nazario-Gonzalez
*Attorney, Agent, or Firm*—Marianne H. Michel

[57] ABSTRACT

A Process is disclosed comprising reacting an alkali metal salt of Z with $MX_4$ to form a trihalo compound; reacting the trihalo compound with an alkali metal salt of Z' to form a dihalo compound; and reacting the dihalo compound with at least one alkali metal organic compound to form $Z-MR_2-Z'$, where Z is a substituted or unsubstituted fluorenyl radical, M is Ge, Si, or Sn, X is Cl, Br, F, or I, each R is a hydrocarbyl radical containing 1 to 20 carbon atoms, and Z' is an unsubstituted cyclopentadienyl, substituted cyclopentadienyl, unsubstituted indenyl, substituted indenyl, unsubstituted fluorenyl, or a substituted fluorenyl. Also new fluorene compounds are disclosed.

33 Claims, No Drawings

FLUORENE COMPOUNDS AND METHODS FOR MAKING

The present invention relates to fluorene compounds. In another aspect, this invention relates to methods for making fluorene compounds.

BACKGROUND OF THE INVENTION

The term "fluorene" as used herein refers to the tricyclic compounds which are generally illustrated by the following structural formula:

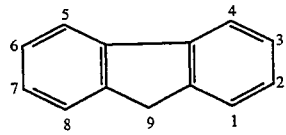

In the chemical names used herein, the position of substituents on the fluorene will be indicated by referring to the point of attachment on the ring carbon by the number system illustrated in the above formula. Unless otherwise indicated, the term fluorenyl as used herein refers to the 9-fluorenyl radical.

Fluorene compounds have found a number of uses in the past. Some such compounds have been found, particularly useful for preparing metallocene compounds which have utility as catalysts for the polymerization of olefins.

It would therefore be desirable to provide a relatively simple process employing one common starting material, where such process is suitable for producing a variety of fluorene compounds. It would also be desirable to provide a process to prepare such compounds where the compounds are separated in substantially pure form.

SUMMARY OF THE INVENTION

An object of the present invention is to provide a new method for preparing certain fluorene compounds.

Another object is to provide methods which can produce fluorene compounds that are more readily obtained in substantially pure form.

Another object is to provide certain new fluorene compounds.

In accordance with the present invention there is provided a process comprising (1) reacting an alkali metal salt of Z with $MX_4$ to produce a trihalo compound, (2) reacting the trihalo compound with an alkali metal salt of Z' to produce a dihalo compound, and (3) reacting the dihalo compound with at least one alkali metal organic compound to produce $Z-MR_2-Z'$, wherein Z is an unsubstituted fluorenyl or substituted fluorenyl, Z' is an unsubstituted cyclopentadienyl, a substituted cyclopentadienyl, an unsubstituted indenyl, a substituted indenyl, an unsubstituted tetrahydroindenyl, a substituted tetrahydroindenyl, an unsubstituted fluorenyl, or a substituted fluorenyl; M is germanium, silicon, or tin; X is a halogen; and each R is an individually selected hydrocarbyl radical containing 1 to 20 carbon atoms.

In accordance with another aspect of the present invention there are provided new fluorene compounds.

DETAILED DESCRIPTION OF THE INVENTION

The Z radical is an unsubstituted fluorenyl or substituted fluorenyl. The currently preferred Z radical is an unsubstituted fluorenyl radical.

Z' is an organic radical having cyclopentadienyl functionality and is an unsubstituted cyclopentadienyl, substituted cyclopentadienyl, unsubstituted indenyl, substituted indenyl, unsubstituted fluorenyl, substituted fluorenyl, unsubstituted tetrahydroindenyl, substituted tetrahydroindenyl, or cyclopentadienyl compound having additional condensed saturated or unsaturated ring systems with or without heteroatoms such as N, P, Si, O, or Sn in the ring system. The currently preferred Z' radical is a cyclopentadienyl radical.

Z or Z' can contain one or more substituents. The substituents on Z or Z' can be the same or different and can vary over a wide range and can be basically any substituent which does not interfere with the method of the present invention. Typical substituents include alkyl substituents containing 1 to 20 carbon atoms, preferably 1 to 10 carbon atoms, and more preferably 1 to 6 carbon atoms. Some examples of substituents include methyl, ethyl, propyl, butyl, tert-butyl, and cyclohexyl. It is also within the scope of the present invention to have the Z or Z' component have substituents which join to form another cyclic ring, especially a $C_4$-$C_6$ ring.

Typically the alkali metal salt of Z can be prepared by dissolving the precursor for the Z radical in a suitable liquid diluent and then adding an alkali metal alkyl. Techniques of forming such salts are known in the art.

The alkali metal alkyls employed in preparing the alkali metal salt of Z include any alkali metal alkyls capable of forming a suitable alkali metal salt of Z. Typically the alkali metal alkyls would be selected from the alkyls of sodium, potassium, and lithium and the alkyl radical would have 1 to 8, preferably 1 to 6 carbon atoms. The preferred alkali metal alkyls are lithium alkyls. Due to availability and efficacy, butyl lithium is especially preferred.

Typical diluents employed in preparing the alkali metal salt of Z include polar diluents such as for example tetrahydrofuran, or non-polar diluents such as alkanes, cycloalkanes, aromatic hydrocarbons and ethers. Some specific examples include toluene, heptane, hexane, and diethylether.

In preparing the alkali metal salt of Z, the molar ratio of the alkali metal alkyl to the precursor of the Z radical will generally be in the range of from about 1:1 to about 50:1.

The alkali metal salt of Z is then reacted with the metal tetrahalide to produce a trihalo compound $Z-MX_3$, also represented by the formula

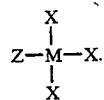

Suitable metal tetrahalides include germanium tetrachloride, germanium tetrabromide, germanium tetrafluoride, germanium tetraiodide, silicon tetrachloride, silicon tetrabromide, silicon tetrafluoride, silicon tetraiodide, stannic tetrachloride, stannic tetrabromide, stannic tetraiodide, and stannic tetrafluoride. Germanium tetrachloride is presently preferred.

The molar ratio of the alkali metal salt of Z to the metal tetrahalide compound can vary over a wide range. The molar ratio will generally be in the range of from about 0.1:1 to about 10:1, preferably from 0.5:1 to 5:1, and more preferably 0.5:1 to 2.5:1.

The trihalo compound is then reacted with an alkali metal salt of Z' to produce a dihalo compound Z-MX$_2$-Z', also represented by the formula

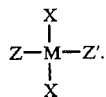

The alkali metal salt of Z' can be prepared in the same manner as described above for the preparation of the alkali metal salt of Z. The currently preferred alkali metal salt of Z' is cyclopentadienyl sodium.

The molar ratio of the alkali metal salt of Z' to the trihalo compound can also vary over a wide range depending on the reactants employed. The molar ratio will generally be in the range of from about 0.1:1 to about 10:1, preferably from 0.5:1 to 5:1, and more preferably 0.5:1 to 2.5:1.

The dihalo compound is then reacted with at least one alkali metal organic compound to produce a fluorene compound Z-MR$_2$-Z', also represented by the formula.

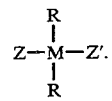

where each R is individually selected and is a hydrocarbyl radical containing 1 to 20 carbon atoms.

The alkali metal organic compound contains a hydrocarbyl radical containing 1 to 20 carbon atoms and is an alkyl, cycloalkyl, aryl radical. Preferably the hydrocarbyl radical contains from 1 to 12 carbon atoms, more preferably from 1 to 8 carbon atoms. The alkali metal in the alkali metal organic compound is sodium, potassium, or lithium. It is also within the scope of the invention to employ a mixture of more than one alkali metal organic compound. The presently preferred alkali metal organic compound is phenyllithium.

The molar ratio of the alkali metal organic compound to the metal dihalo compound can also vary over a wide range depending on the reactants employed. The molar ratio will generally be in the range of from about 0.1:1 to about 10:1, preferably from 0.5:1 to 6:1, and more preferably 0.5:1 to 4:1.

The reaction pressure and temperatures for the processes disclosed herein are not particularly critical and can vary over a wide range depending upon the results desired. Atmospheric pressures are currently preferred, although higher or lower pressure could be employed. Typically, the reaction temperatures will be in the range of about −100° C. to about 100° C. Generally it is convenient to carry out the reactions at ambient temperature.

Typically the reactions disclosed herein are carried out in the presence of a suitable liquid diluent, such as those described above for the preparation of the alkali metal salt of Z.

The present compounds are useful for preparing metallocene catalysts for the polymerization of aliphatic mono-1-olefins. The metallocene catalysts are especially useful for producing stereoregular polymers. While the invention would appear to be suitable for use with any aliphatic mono-1-olefin, those olefins having 2 to 18 carbon atoms are most often used. Aliphatic mono-1-olefins can be copolymerized with other 1-olefins.

Other applications for metallocene catalysts include asymmetric hydrogenation, alkene epoxidation, alkene isomerization, ketone reduction and as stoichiometric reagents for stereoselective cobalt-mediated reactions, allyltitanium addition reactions with aldehydes, and the highly selective formation of allylic amines.

The following example will serve to show the present invention in detail by way of illustration and not by way of limitation.

EXAMPLE

Preparation of cyclopentadienylfluorenyldiphenylgermane

The example demonstrates the effectiveness of the present process for preparing compounds represented by the formula Z-GeR$_2$-Z'. Cyclopentadienylfluorenyldiphenylgermane was prepared by reacting the trihalo compound, 9-fluorenyltrichlorogermane, with cyclopentadienyl sodium to produce the dihalo compound, cyclopentadienylfluorenyldichlorogermane. The dihalo compound was then reacted with phenyl lithium to produce cyclopentadienylfluorenyldiphenylgermane. The process can be illustrated by the following flow diagram.

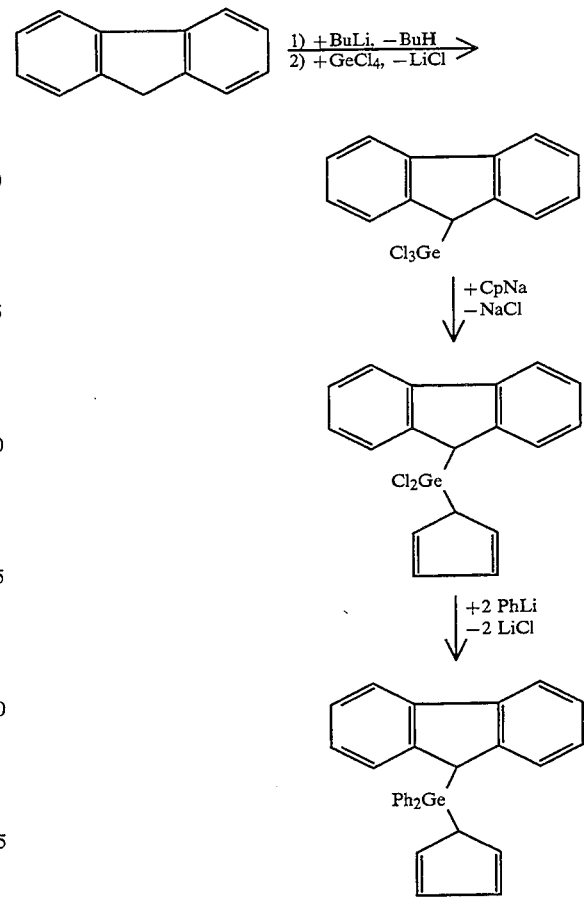

The trihalo compound, fluorenyltrichlorogermane, was prepared by adding 38 mL butyllithium (1.6M in hexane) to a solution of 10 g (0.06M) fluorene in 150 mL of ether. The reaction was continued for 4 hour at room temperature. The ether was then removed by vacuum. The thus produced lithium salt of fluorene was added in portions to a solution of 13 g germanium tetrachloride (0.06M) in 500 mL pentane. The mixture was stirred for 2 hours and then dried in a vacuum. The residue was extracted with methylene chloride and the solution was filtered over sodium sulfate. The solution was evaporated to a volume of 100 mL and long colorless needles of 9-fluorenyltrichlorogermane were crystallized at −30° C. The yield was 85%.

The dihalo compound, was prepared by reacting 5 g (14.5 mmol) 9-fluorenyltrichlorogermane suspended in 100 mL of ether with 1.4 g (16 mmol) cyclopentadienyl sodium, the mixture was stirred for 12 hours at room temperature and then dried in vacuum. The thus produced dihalo compound in the form of a white residue was extracted with dichloromethane and the solution was filtered over sodium sulfate to remove sodium chloride.

The compound, $Z$-$GeR_2$-$Z'$, was prepared by reacting 2 g (5.4 mmol) of the dihalo product suspended in 150 mL ether with 1.3 g (16 mmol) phenyllithium. The reaction mixture was stirred for 12 hours at room temperature. The solvent was then removed by means of a vacuum. The greenish residue was extracted with dichloromethane and the suspension was filtered over sodium sulfate to remove lithium chloride. The solvent was evaporated and the residue was washed several times with pentane and then dried in a vacuum. The thus produced 1-cyclopentadienyl-9-fluorenyldiphenylgermane product was a bright yellow powder and gave 85–90% yield.

That which is claim is:

1. A process comprising:
   (1) reacting an alkali metal salt of Z with $MX_4$ to produce a trihalo compound,
   wherein Z is an unsubstituted fluorenyl or a substituted fluorenyl, M is Ge, Si, or Sn, and X is Cl, Br, F, or I:
   (2) reacting said trihalo compound with an alkali metal salt of Z' to produce a dihalo compound,
   wherein Z' is an unsubstituted cyclopentadienyl, substituted cyclopentadienyl, unsubstituted indenyl, substituted indenyl, unsubstituted tetrahydroindenyl, substituted tetrahydroindenyl, unsubstituted fluorenyl, or a substituted fluorenyl
   wherein substituents on substituted Z or Z' can be the same or different and are alkyl radicals containing from 1 to 20 carbon atoms; and
   (3) reacting said dihalo compound with at least one alkali metal organic compound to produce $Z$-$MR_2$-$Z'$,
   wherein each R is individually selected and is a hydrocarbyl radical containing 1 to 20 carbon atoms.

2. A process according to claim 1 wherein Z is an unsubstituted fluorenyl radical.

3. A process according to claim 1 wherein M is Ge.

4. A process according to claim 1 wherein X is Cl.

5. A process according to claim 1 wherein Z' is a cyclopentadienyl radical.

6. A process according to claim 1 wherein each R is an alkyl, cycloalkyl, or aryl radical containing 1 to 12 carbon atoms.

7. A process according to claim 6 wherein each R contains 1 to 8 carbon atoms.

8. A process according to claim 6 wherein each R is an aryl radical.

9. A process according to claim 8 wherein each R is a phenyl radical.

10. A process according to claim 1 wherein said alkali metal salt of Z is a lithium fluorenyl compound.

11. A process according to claim 1 wherein said alkali metal salt of Z' is a sodium cyclopentadienyl compound.

12. A process according to claim 1 wherein said Z' is an unsubstituted cyclopentadienyl radical.

13. A compound of the formula $Z$-$MR_2$-$Z'$ produced by the process of claim 1, wherein M is Ge or Sn.

14. A process comprising:
   (1) reacting an alkali metal salt of Z with $GeCl_4$ to produce a trihalo compound,
   wherein Z is an unsubstituted fluorenyl radical;
   (2) reacting said trihalo compound with an alkali metal salt of Z' to produce a dihalo compound,
   wherein Z' is an unsubstituted cyclopentadienyl radical; and
   (3) reacting said dihalo compound with at least one alkali metal organic compound to produce $Z$-$GeR_2$-$Z'$,
   wherein each R is an alkyl, cycloalkyl, or aryl radical containing 1 to 8 carbon atoms.

15. A process according to claim 14 wherein each R is a phenyl radical.

16. A process according to claim 14 wherein each R is a methyl radical.

17. A compound of the formula

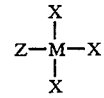

wherein Z is a substituted or unsubstituted fluorenyl,
M is Ge, or Sn, and
X is Cl, Br, F, or I.

18. A compound according to claim 17 wherein Z is an unsubstituted fluorenyl radical.

19. A compound according to claim 17 wherein M is Ge.

20. A compound according to claim 17 wherein X is Cl.

21. A compound of the formula

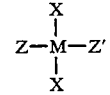

wherein Z is a substituted or unsubstituted fluorenyl,
M is Ge, Si, or Sn, and
X is Cl, Br, F, or I,
wherein Z' is an unsubstituted cyclopentadienyl, substituted cyclopentadienyl, unsubstituted indenyl, substituted indenyl, unsubstituted fluorenyl, or a substituted fluorenyl, and wherein substitutents on substituted Z or Z' can be the same or different and are alkyl radicals containing from 1 to 20 carbon atoms.

22. A compound according to claim 21 wherein Z is an unsubstituted fluorenyl radical.

23. A compound according to claim 21 wherein M is Ge.

24. A compound according to claim 21 wherein X is Cl.

25. A compound according to claim 21 wherein Z' is an unsubstituted cyclopentadienyl.

26. A compound of the formula Z-MR$_2$-Z':
wherein Z is a substituted or unsubstituted fluorenyl;
M is Ge or Sn;
Z' is an unsubstituted cyclopentadienyl, substituted cyclopentadienyl, unsubstituted indenyl, substituted indenyl, unsubstituted fluorenyl, or a substituted fluorenyl; and
wherein each R is an individually selected hydrocarbyl radical and is an alkyl, cycloalkyl, or aryl radical containing 1 or 20 carbon atoms, and wherein substitutents on substituted Z or Z' can be the same or different and are alkyl radical containing from 1 to 20 carbon atoms.

27. A compound according to claim 26 wherein z is an unsubstituted fluorenyl radical.

28. A compound according to claim 26 wherein M is Ge.

29. A compound according to claim 26 wherein said Z' is an unsubstituted cyclopentadienyl radical.

30. A compound according to claim 26 wherein each R contains 1 to 12 carbon atoms.

31. A compound according to claim 30 wherein each R contains 1 to 8 carbon atoms.

32. A compound according to claim 31 wherein each R is an aryl radical.

33. A compound according to claim 32 wherein each R is a phenyl radical.

* * * * *